(12) United States Patent
Keränen

(10) Patent No.: US 11,344,416 B2
(45) Date of Patent: May 31, 2022

(54) MEDICAL ARRANGEMENT FOR INTRODUCING AN OBJECT INTO AN ANATOMICAL TARGET POSITION

(71) Applicant: Medtentia International Ltd Oy, Espoo (FI)

(72) Inventor: Olli Keränen, Bjärred (SE)

(73) Assignee: Medtentia International Ltd Oy, Espoo (FI)

( * ) Notice: Subject to any disclaimer, the term of this patent is extended or adjusted under 35 U.S.C. 154(b) by 47 days.

(21) Appl. No.: 16/742,974

(22) Filed: Jan. 15, 2020

(65) Prior Publication Data
US 2021/0212829 A1 Jul. 15, 2021

(51) Int. Cl.
*A61F 2/24* (2006.01)

(52) U.S. Cl.
CPC .... *A61F 2/2466* (2013.01); *A61F 2220/0016* (2013.01)

(58) Field of Classification Search
CPC .... A61F 2/2442; A61F 2/2445; A61F 2/2448; A61F 2/2454; A61F 2/2457; A61F 2/246; A61F 2/2466; A61F 2230/0091; A61F 2250/006
See application file for complete search history.

(56) References Cited

U.S. PATENT DOCUMENTS

2015/0100117 A1* 4/2015 Bortlein ........... A61B 17/00234
623/2.11
2018/0296798 A1* 10/2018 Lepak ............... A61M 25/0136

* cited by examiner

*Primary Examiner* — Brian A Dukert
*Assistant Examiner* — Rebecca Lynee Zimmerman

(57) ABSTRACT

A medical arrangement is configured to introduce an object, such as an implant, from a distal end into an anatomical target position. The medical arrangement comprises a first introducer having distal and proximal ends, and a second introducer having distal and proximal ends. The first introducer is an outer introducer and said second introducer is configured to be operated inside and guided by said first introducer. At least a portion of the first introducer is configured to take a first curved shape, and at least a portion of the second introducer is configured to take a second curved shape. The portion of the second introducer configured to take said second curved shape comprises a tubular member inside said second introducer for enabling introducing of the object or implant through said tubular member and thereby over at least said second curved shape of said second introducer.

14 Claims, 3 Drawing Sheets

MEDICAL ARRANGEMENT FOR INTRODUCING AN OBJECT INTO AN ANATOMICAL TARGET POSITION

TECHNICAL FIELD OF THE INVENTION

The invention relates to a medical arrangement for introducing an object, such as an implant with spikes or other sharp protrusion into an anatomical target position. The implant may be for example a cardiac implant (like an annuloplasty medical device) and the anatomical target position an annulus of a heart valve, such as a mitral valve or tricuspid valve.

BACKGROUND OF THE INVENTION

FIG. 1A illustrates a portion of the heart 12, the mitral valve 18, and the left ventricle 14 as an example of the anatomical target position. The mitral valve is at its boundary circumferenced by an annulus 20. The valve has two cusps or leaflets 22, 24. Each of these cusps or leaflets 22, 24 are connected to a respective papillary muscle 27, 29 via their respective connecting chordae 26, 28. In normal healthy individuals the free edges of the opposing leaflets will close the valve by coaptation. However, for some individuals the closure is not complete, which results in a regurgitation, also called valvular insufficiency, i.e. back flow of blood to the left atrium making the heart less effective and with potentially severe consequences for the patient. FIG. 1B illustrates a mitral valve 18, in which the leaflets 22, 24 do not close properly. This commonly occurs when the annulus 20 becomes dilated. One surgical procedure to correct this is to remove a portion of the leaflet 24 and stitch the cut edges together with one another. The procedure will pull back the annulus 20 to a more normal position. However the strength of the leaflet 24 is altered. Similar problems with a less effective heart function occur if one or both leaflets are perforated to such an extent that blood is flowing towards the left atrium, although the leaflets close properly.

In some conditions of degenerated heart function, the leaflets do not present a solid surface, as in a degenerative valve disease. The leaflet may also be ruptured, most commonly at an edge of a leaflet, resulting in an incomplete coaptation. Hence, cardiac devices and methods are developed for repairing of one or more leaflets of a heart valve, or other related anatomical structures, such as the chordae attached to the ventricular side of leaflets.

FIGS. 2A and 2B illustrate exemplary implants to be delivered and introduced into an anatomical target position, and in particularly a cardiac implant 110. The implant may comprise one or more loop-shaped structures 111, 112. Advantageously one first loop-shaped structure is configured to abut a first side 20A of the heart valve and one second loop-shaped structure is configured to abut a second, opposite, side 20B of the valve to thereby trap a portion of the valve tissue 20 between the second and the first support structures 111, 112. The implant 110 may have teeth 113 in order to keep the implant in its position after introduction to the anatomical target position.

The implant is typically delivered via one or more introducers and has thus usually a delivery state, where the implant has an elongated form. The first introducer is delivered into a first extent and the second introducer to a second extend being closer or next to the anatomical target position. The first introducer provides a first curve advantageously in its distal end portion and the second introducer a second curve in its distal end portion. Also, more than two introducers can be used.

The implant comprises typically a shape memory material having a first shape, such as the elongated form of the delivery state in a first temperature, and the second shape, such as the loop-shaped form in a second temperature. The second temperature corresponds advantageously essentially the body temperature, whereupon the implant takes the second shape, corresponding the loop-shaped form, when introduced for example with the blood flow in the atrium.

However, some problems arise in particularly when the object with sharp protrusions, such as the implant with teeth, is introduced via introducers into the anatomical target position, namely the sharp protrusions will easily claw the inner surface of the second or further (innermost) introducer. This causes that the object gets easily stuck into the second introducer and in addition the object tends move also the second introducer. Furthermore, the object easily grates the soft inner wall surface of the second introducer, thereby releasing microscopic grains of the inner wall material, which is highly unwanted phenomenon, because the microscopic grains might be carried to the anatomical target position of the patient. In particularly this tends to happen in a portion where there is a curve in the innermost introducer so where the introducer is bend.

SUMMARY OF THE INVENTION

It is an object of the invention to alleviate and eliminate the problems relating to the known prior art. Especially the object of the invention is to provide a medical arrangement for introducing an object, in particularly an implant with sharp protrusions, such as teeth, into an anatomical target position in an easy, fast, safe and accurate manner so that the object would slide easily without getting stuck into the curve portion of the catheter. In addition, an object of the invention is to introduce the object through the introducer so that the sharp protrusions of the object would not extract or release any inner wall material from the introducer to the anatomical target position.

The object of the invention can be achieved by the features of the annexed claims.

The invention relates to a medical arrangement for introducing an object, such as an implant with teeth or spikes, into an anatomical target position, such as a cardiac implant into an annulus of a heart valve, as claimed.

A medical arrangement according to the invention is configured to introduce an object with sharp protrusions, such as an implant with teeth, into an anatomical target position. In particularly the invention is configured to introduce a cardiac implant, or an annuloplasty medical device with teeth, from a distal end of the arrangement into an anatomical target position, such as into an annulus of a heart valve. The heart valve may be a mitral valve or tricuspid valve, for example, not limiting to those only.

According to an example the object is the implant, which comprises in a use a loop shaped support portion, having either one or more loops or coils so that one first loop-shaped structure can be configured to abut a first side of the heart valve and one second loop-shaped structure to abut a second, opposite, side of the valve to thereby trap a portion of the valve tissue between the second and the first support structures. It is also possible that there is only the one first loop-shaped structure, which is configured to abut a first side of the heart valve, and not the second support structures, or vice versa. The implant is advantageously adapted to support for a mitral valve upon being fully delivered. Advantageously the implant comprises sharp teeth (as shown in FIG. 2B), which are configured to penetrate to the tissue in the anatomical target position and thereby to keep the implant in its position during use. This might be challenging for example in pulsating environment, such as in the heart, because if the teeth are for example inclined (not perpendicular in relation to a longitudinal axis of the implant), the pulsating movement might cause a rotation of the implant out of its position.

According to an embodiment the medical arrangement comprises a first introducer having distal and proximal ends. The introducer is advantageously configured to be delivered into the anatomical target, such as especially the mitral valve area in or near a mitral plane. In addition, the arrangement comprises also second introducer having distal and proximal ends. The first introducer is an outer introducer and the second introducer is configured to be operated inside and guided by said first introducer. When the first introducer is delivered in or near the mitral plane, the angle of the introducer and thus also the implant is very optimal so that the introducer and thus also the implant will follow the curvature and anatomical shapes of the annulus and heart. Thus, no steep curves for the introducers or implants are needed, whereupon the additional introducers and implant are more easily to delivered. This is because the steep curves increase friction between the introducers as well as inner introducer and the implant, which now can be avoided.

According to the invention at least a portion, advantageously in a distal portion, of the first introducer is configured to take a first curved shape. In addition, at least a portion, advantageously in a distal portion, of the second introducer is configured to take a second curved shape. Advantageously said first and second curved shapes are concentric curved shapes so that all the curves are curved in the same hand direction and thus form a helical loop structure.

The first introducer is advantageously configured to take said first curved shape when said first introducer is delivered towards or into said anatomical target position. The second introducer is configured to take said second curved shape to the same hand direction as the first curved shape of the first introducer when said second introducer is introduced from the distal end portion of the first introducer. Also, a third introducer can be used with same (concentric) curvature direction and so that it takes a third curved shape to the same hand direction as the previous first and second ones. The curved shape can be taken for example so that there is an operating wire (or the like) arranged to elongate between the proximal and distal ends of the introducer and along a side to which said curved shape is to be provided, whereupon when the operating wire is tightened advantageously from the proximal end of the introducer, it will cause the introducer in question to bend to that direction. There is advantageously a flexible portion arranged inside and/or outside the curve and into a casing of the introducer so that when the operating wire is tightened, said introducer is caused to take said curved shape at the point of said flexible portion and to said direction said flexible portion locates. The flexible portion can be for example a cutting, such as for example a laser cutting, but also other techniques can be used, such as material weakening, like thinning the wall of the introducer inside and/or outside the curve. Typically, the introducer (catheter) comprise number of polycarbonate layers, for example, whereupon the weakening can be used via material technique for the layers. In addition, the operating wire is typically integrated between the layers. According to embodiment also memory materials can be used causing bending of the distal end of the introducer.

According to an advantageous embodiment of the invention at least the curved portion of the second introducer (or further, advantageously the innermost and nearest introducer to the anatomical target position during use) comprises a tubular member inside the introducer. The tubular member may advantageously comprise a circular profile, such as C-profile or O-profile. The tubular member may be a separate tubular tube or trough (C-profile), which is introduced into the second introducer before introducing the implant, so before the use. Alternatively, the tubular member may be integrated, such as coated, laminated, glued or welded, into an inner wall of the second introducer and in particularly into an area of the second curve shape of the second introducer. The tubular member may be for example integrated as a laminated layer during a manufacturing process of the introducer to its inner wall surface.

The tubular member comprises advantageously a metallic or carbon fibre inner surface at least at the portion of the second curved shape and at least on the outer, upper and/or lower curve portion of the tubular member when curved along the second curved shape of said second introducer. According to an example the tubular member is a metallic tube or metallic trough (C-profile). Also, other suitable hard material can be used, such as carbon fibre, so that the sharp protrusions of the object is not able to penetrate through the inner surface layer of the introducer and get thereby stuck and in addition is not able to release inner wall material of the introducer.

It is to be noted that also C-profile tubular member can be used so that it covers outer, upper and lower walls of the curve portion. The opening of the C-profile can be pointed towards the inner curve, namely the sharp distal end of the implant will hit the outer curve, and the sharp teeth of the implant (as described in FIG. 2B, for example) will touch upper and lower walls of the curve portion (the teeth of the implant described in FIG. 2B are arranged both in the upper and lower portions of the implant).

The tubular member enables introducing the object, such as the implant with teeth, through the tubular member and thereby over at least the second curved shape of the second introducer, namely the sharp protrusions of the object are not able to penetrate to the inner wall of the tubular member, which is much hard coating than the introducer, which is typically soft and sloppy.

It is to be noted that even if the second introducer is described here to receive the tubular member, it might also be another introducer, such as third or fourth etc. introducer, depending on an application how many introducers are applied. In practise, the introducer in question to receive the tubular member is the innermost one whose distal end is nearest to the anatomical end target portion during use, and which guides the implant to the utmost anatomical end target portion.

According to an embodiment the tubular member comprises a cutting section having cuttings, such as laser cuttings, allowing the tubular member bend into the same centric direction as the second introducer, so i.e. the distal end portion of the innermost introducer. The cuttings are advantageously arranged at least outside of the curve of the tubular member into an area, which will be curved along the second curved shape of the second introducer during use.

According to an embodiment, the ends of two adjacent cuttings in a first side of the tubular member are non-aligned so that they are not in the same level in the axial plane of the tubular member, where the axial plane is a plane being parallel with the longitudinal axis of the tubular member and the second introducer. In addition, according to an embodiment the ends of every second or third cuttings of the tubular member are aligned.

However, in the second opposite side of the tubular member, the ends of the cuttings are aligned so to form a longitudinal non-cut portion. The longitudinal non-cut portion is parallel with the longitudinal axis of the tubular member. The longitudinal non-cut portion forms advantageously a spinal column allowing the tubular member to bend in a first direction (the same hand direction as the curve shape of the second introducer), but resist the bending to the opposite direction.

It is to be noted that the cutting section, as the whole tubular member, is advantageously non-stretchable. In addition, the tubular member may comprise a smooth cutting section, as a transition section, next to the cutting section and towards the proximal end of the second introducer. This will provide smoother transition from the essentially non-flexible tubular member portion to more flexible portion offered by the cuttings, whereupon e.g. stresses induced to the tubular member in the curve portion can be kept minimal, thereby improving durability of the tubular member and avoiding sharp edge between the non-flexible and flexible portions. In addition, the object will slide even more smoother when the flexibility of the tubular member in the curve area changes with smaller steps.

According to an embodiment the cuttings are inclined from a radial plane of the tubular member being perpendicular to the longitudinal axis of the tubular member. The inclination is advantageously between 5°-20° and is advantageously about 10°. The inclination allows or forces the distal end of the tubular member to turn downwards or upwards from the axial plane of the transition section of the tubular member, such as downwards or upwards from a mitral plane, when used in mitral valve operations.

As an example, the anatomical target position is a left atrium or left ventricle or an annulus area of a mitral valve. In this case the first introducer is advantageously delivered into a first side of the annulus of the mitral valve and essentially in the mitral plane or in an angle less than in relation to the mitral plane. The second (or further) introducer is then delivered to the second side of the annulus of the mitral valve between leaflets said second side of the annulus being opposite to said first side.

The present invention offers advantages over the known prior art, such as an easy, safe, precise and time saving manner to reliable delivering the object with sharp protrusions, such as an implant with teeth to the anatomical target position, like to the annulus of the heart valve. Due to the tubular member the object can be delivered in a smooth way over the curves of the catheter(s) so that any sharp protrusions do not grab to the wall structure of the innermost catheter, in particularly in any curve portion.

The exemplary embodiments presented in this text are not to be interpreted to pose limitations to the applicability of the appended claims. The verb "to comprise" is used in this text as an open limitation that does not exclude the existence of also un-recited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which.

DETAILED DESCRIPTION

Figure 1A:
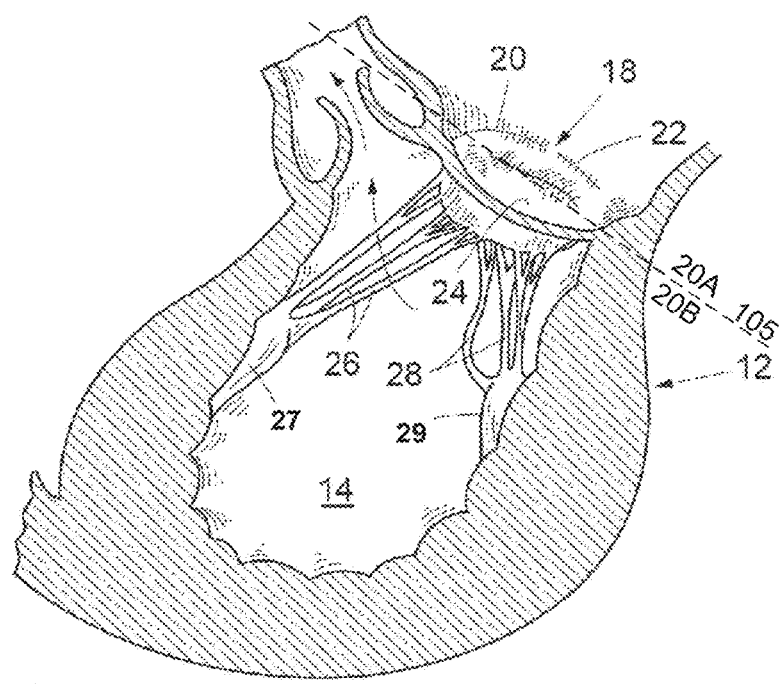
FIGS. 1A-1B illustrate schematically a portion of a heart and mitral valve.
Figure 1B:
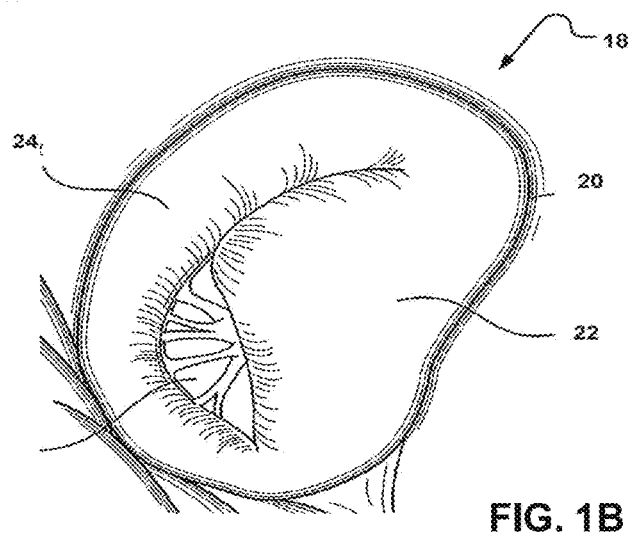
Figure 2A:
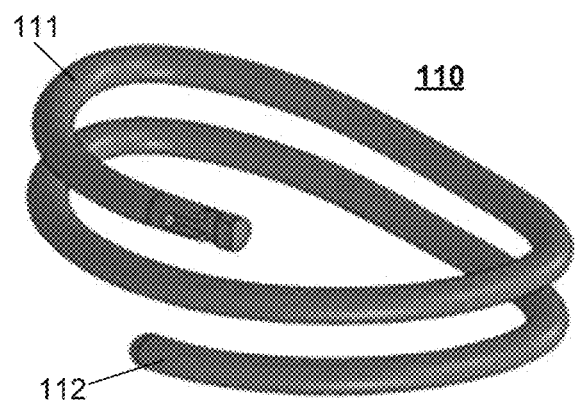
FIGS. 2A-2B illustrate exemplary implants.
Figure 2B:
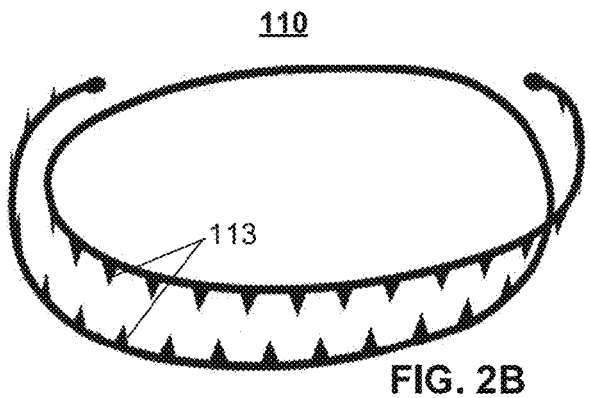

FIGS. 1A-1B and 2A-2B are already discussed in more details in connection with the background of the invention portion above.

FIGS. 3-6 illustrate a medical arrangement 100 for introducing an implant 110 into an anatomical target position according to advantageous embodiments of the invention, where the medical arrangement 100 comprises a first introducer 101 having distal and proximal ends 101A, 101B. The introducer is advantageously configured to be delivered into the mitral valve area in a mitral plane 105 or in an angle 101E advantageously less than 45° and more advantageously less than less than 30° in relation to the mitral plane 105. In addition, the arrangement comprises also second introducer 102 having distal and proximal ends 102A, 102B.

Figure 3:
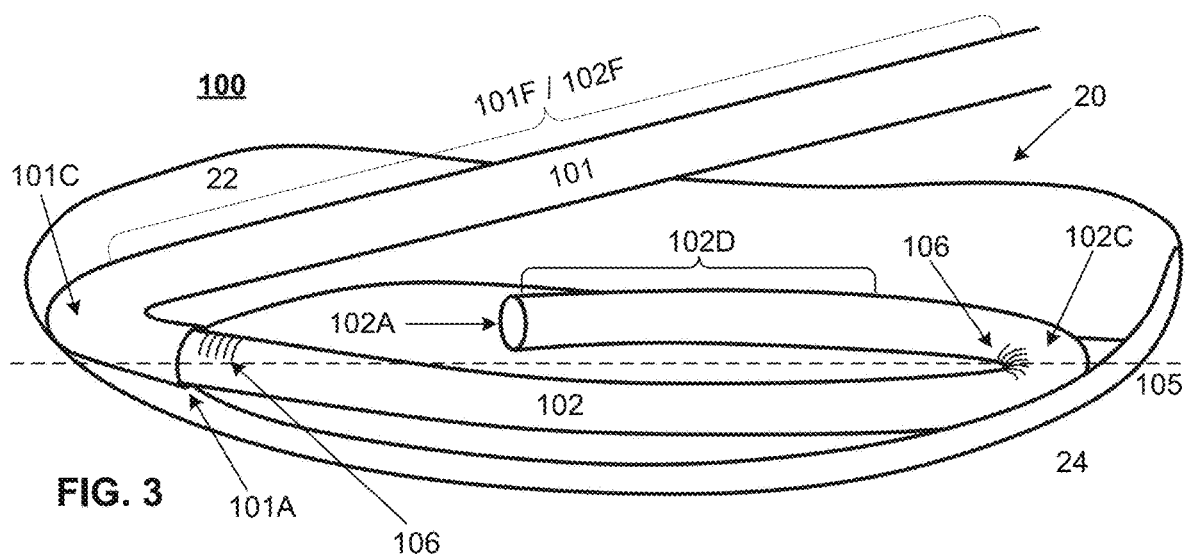
FIGS. 3, 4, 5A-F, and 6 illustrate a medical arrangement for introducing an implant into an anatomical target position according to advantageous embodiments of the invention.

The first introducer 101 is delivered first in a straightened configuration 101F until the distal end 101A of the first introducer 101 reaches its extent towards the anatomical target position, whereupon the distal portion is configured to take the first curved shape 101C, advantageously following the anatomical shapes of the anatomical target position. It is to be noted that the first introducer 101 does not typically go further, but after this the second introducer 102 is delivered inside the first introducer 101 in a straightened configuration 102F. The second introducer 102 follows the shapes of the first introducer 101 until it comes out from the distal end 101A of the first introducer 101, after which the second introducer 102 is still delivered further until the distal portion of the second introducer 102 is configured to take the second curved shape 102C, as can be seen in FIG. 3.

Figure 4:
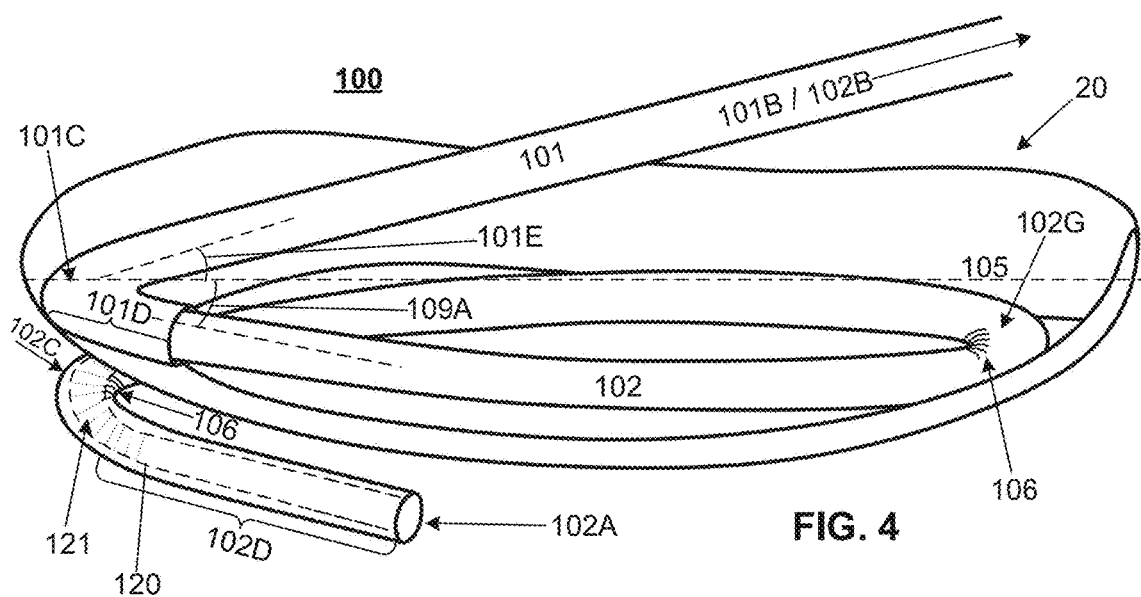

According to an example the second introducer 102 can still be delivered further until the distal portion of the second introducer 102 is configured to take the additional curved shape 102G, as can be seen in FIG. 4. The additional curved shape 102G locates to the direction of the proximal end 102B from the second curved shape 102C. However, it is to be noted that the additional curved shape 102G is optional, for example if third or more introducers are used (not shown in this document).

Advantageously the second introducer 102 (possibly also the first introducer 101) comprises a flexible portion 106 so that said introducer 101, 102 takes said curved shape 101C, 102C at the point of said flexible portion 106 to the direction where the flexible portion 106 locates. The flexible portion 106 can be a cutting, in particularly a laser cutting, for example or achieved by material weakening, like thinning. The flexible portion 106 is arranged into a casing of the introducer 101, 102 and so that it is left inside the curve when the introducer takes said curve shape.

Figure 6:
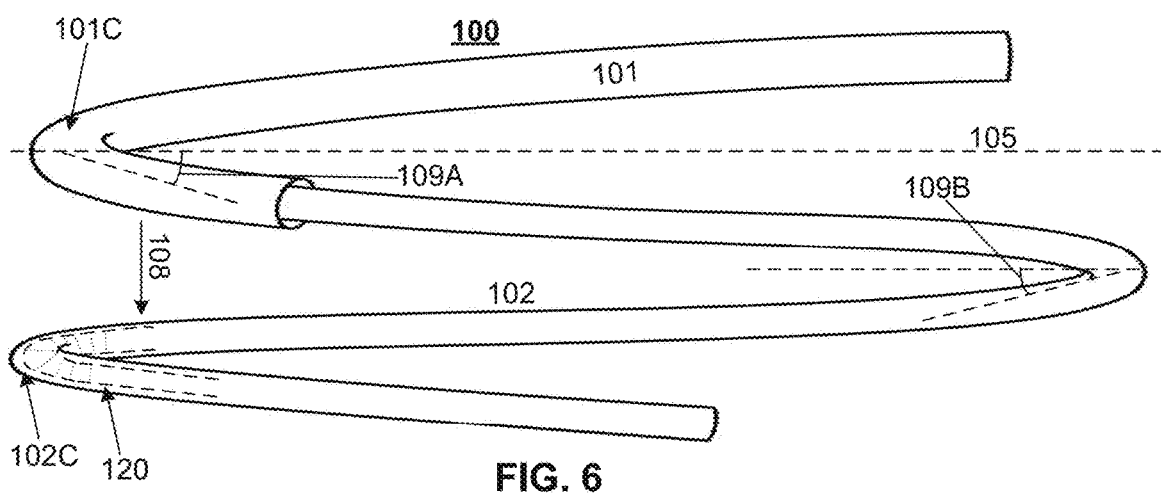

It is to be noted that the first and second curved shapes turn the first and second introducers 101, 102 concentrically essentially in the mitral plane 105. However, as can be seen in FIGS. 3, 4 and 6, for example, the first and second introducers 101, 102 are also configured to tilt or bank downwards 108 and thereby form an angle 109A, 109B also downwards 108. Therefore, when the introducers are delivered for example to the left ventricle, the introducers take a helical loop form due to said first and second and additional curved shapes 101C, 102C, 102G, but in addition to this the distal end portion of the first introducer 101, and advantageously also the second introducer 102 takes the angle downwards 108, whereupon at least the second (or third, if used) introducer 102 can be delivered to the opposite side of the annulus and so that the introducers still follow smoothly the shapes of the anatomical target position.

Figure 5A:
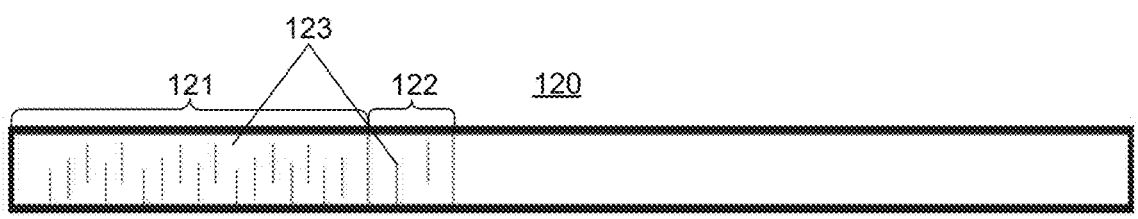
Figure 5B:
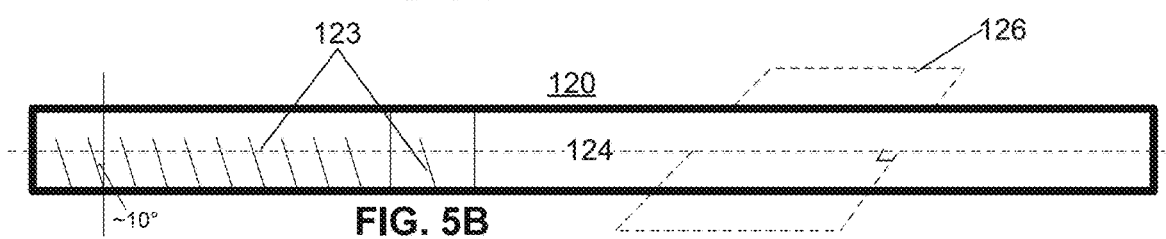

As can be seen in FIGS. 4 and 6, the second introducer 102 comprises a a tubular member 120 inside the introducer (not shown in other Figures). FIGS. 5A and 5B illustrate exemplary tubular members 120 with a cutting section 121 having cuttings 123. The cuttings 123 may be arranged perpendicular to the longitudinal axis 124 of the tubular member 120, as is the case in FIG. 5A, or the cuttings 123 may be inclined or tilted from a radial plane 125 of the tubular member, where the radial plane 125 is perpendicular to the longitudinal axis 124 of the tubular member 120. The inclination is advantageously between 5°-20° and is advantageously about 10°.

The tubular member advantageously comprises also a smooth cutting section, as a transition section 122, next to the cutting section 121 and towards the proximal end of the second introducer during use.

Figure 5C:
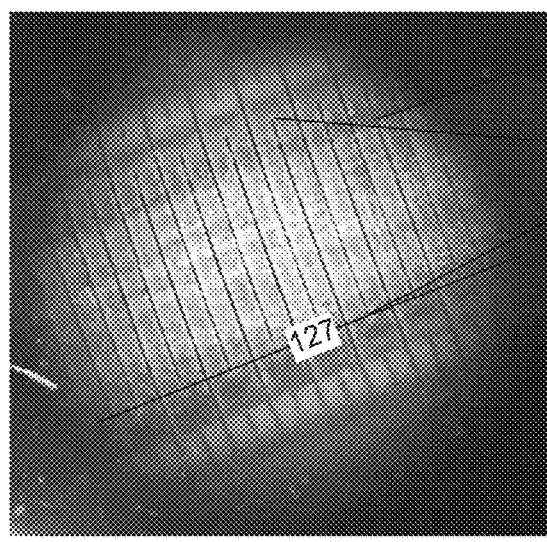
Figure 5D:
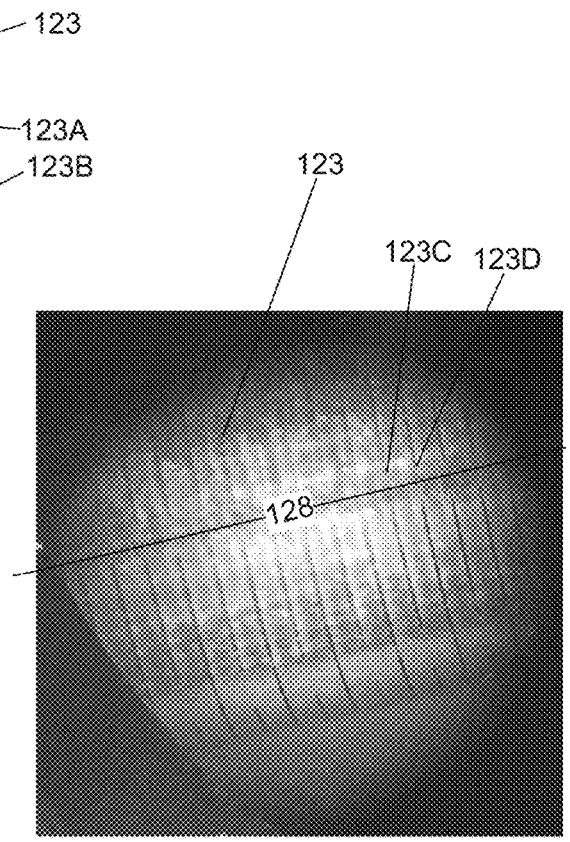

FIG. 5C illustrates a first side of the tubular member 120, where the ends of two adjacent cuttings 123 are non-aligned so that they are not in the same level 127 in the axial plane 126 of the tubular member, where the axial plane 126 is a plane being parallel with the longitudinal axis 124 of the tubular member 120 and the second introducer. In the example of FIGS. 5C and 5D the ends 123A, 123B of every second cuttings 123 of the tubular member 120 are aligned.

FIG. 5D illustrates a second opposite side of the tubular member 120, where the ends of the cuttings 123C, 123D are aligned so to form a longitudinal non-cut portion 128 parallel with the longitudinal axis 124 of the tubular member 120. The longitudinal non-cut portion 128 forms a spinal column allowing the tubular member to bend in a first direction (the same hand direction as the curve shape of the second introducer) but resist the bending to the opposite direction.

Figure 5E:
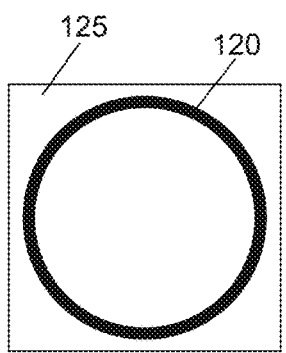
Figure 5F:
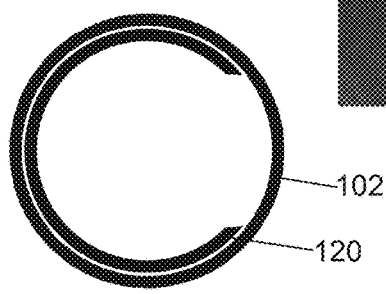

In addition, the tubular member may comprise for example a C-profile (as shown in FIG. 5F) or an O-profile (as shown in FIG. 5E).

The invention has been explained above with reference to the aforementioned embodiments, and several advantages of the invention have been demonstrated. It is clear, that the invention is not only restricted to these embodiments but comprises all possible embodiments within the spirit and scope of the inventive thought and the following patent claims.

In addition, it is to be noted that even if the implant is described in this document as an example to be delivered, also other kinds of object with sharp protrusions can be delivered according to the invention. Furthermore, even if the heart is described in many embodiments, it is to be understood that the heart is only an example of the anatomical target and the invention can be applied also with organ or target positions.

Furthermore, it is to be understood that the cuttings may comprise at least two different lengths, or the cutting may be the same length.

The invention claimed is:

1. A medical arrangement configured to introduce an object or implant from a distal end of the arrangement into an anatomical target position, the medical arrangement comprising:
   a first introducer having distal and proximal ends, and
   a second introducer having distal and proximal ends,
   wherein
   said first introducer is an outer introducer, and said second introducer is configured to be operated inside and guided by said first introducer, and
   at least a portion of the first introducer is configured to take a first curved shape, and at least a portion of the second introducer is configured to take a second curved shape;
   wherein
   said first and second curved shapes are concentric curved shapes,
   at least said portion of the second introducer configured to take said second curved shape comprises a tubular member inside said second introducer for enabling introducing of the object or implant through said tubular member and thereby bypass at least said second curved shape of said second introducer, and
   wherein the tubular member comprises an inner surface, which is harder than an inner surface of the second introducer at least at the portion of said second curved shape.

2. The arrangement of claim 1, wherein the inner surface of the tubular member comprises metal or carbon fibre.

3. The arrangement of claim 1, wherein the tubular member is a round tube or C-profile, where the C-profile covers an outer, upper or lower portion of the second curved shape of the second introducer.

4. The arrangement of claim 3, wherein the tubular member comprises a cutting section having cuttings arranged outside of the curve of the tubular member and allowing the tubular member bend into the same centric direction as said second introducer.

5. The arrangement of claim 4, wherein the cuttings are laser cuttings.

6. The arrangement of claim 4, wherein the ends of two adjacent cuttings in a first side of the tubular member are non-aligned so that they are in different level in relation to an axial plane of the tubular member, where the axial plane is a plane being parallel with the longitudinal axis of the tubular member and the second introducer, and wherein in the second opposite side of the tubular member the ends of the cuttings are aligned so to form a longitudinal non-cut portion enabling the tubular member to bend into a first direction but resisting the bending to opposite direction.

7. The arrangement of claim 4, wherein the cuttings are inclined about 10 degrees from a radial plane being perpendicular to a longitudinal axis of the tubular member.

8. The arrangement of claim 4, wherein the tubular member comprises a transition section next to said cutting section and towards said proximal end of the second introducer, wherein said transition section comprises less number of cuttings in the same area than said cutting section.

9. The arrangement of claim 1, wherein the tubular member is a separate tubular member to be introduced into said second introducer before introducing the implant.

10. The arrangement of claim 1, wherein the tubular member is integrated, coated, glued, laminated or welded into an inner wall of the second introducer and into an area of said second curve shape of the second introducer.

11. The arrangement of claim 1, wherein said portion of the second introducer taking said second curved shape is a distal portion of said second introducer, said distal portion locating between the distal end and proximal end of the second introducer.

12. The arrangement of claim 1, wherein said first introducer is a catheter or an outer steerable catheter, and said second introducer is a steerable catheter.

13. The arrangement of claim 1, wherein said anatomical target position is a left atrium or left ventricle or an annulus area of a mitral valve, whereupon said first introducer is configured to be delivered into a first side of the annulus of the mitral valve essentially in a mitral plane in an angle less than 45° in relation to the mitral plane, whereupon said second introducer is configured to be delivered to a second side of the annulus of the mitral valve between leaflets, said second side of the annulus being opposite to said first side.

14. A method for introducing an object or implant into an anatomical target position, wherein in the method a first introducer is delivered towards or into the anatomical target position, where at least a portion of first introducer takes a first curved shape, a second introducer is delivered towards or into the anatomical target position inside said first introducer, where at least a portion of the second introducer takes a second curved shape when said second introducer is introduced from a distal end of the first introducer, wherein said first and second curved shapes are concentric curved shapes, at least said portion of the second introducer taking said second curved shape comprises, at least during use, a tubular member inside said second introducer, wherein said tubular member guides the object or implant through said tubular member and thereby bypass at least said second curved shape of said second introducer, and wherein the tubular member comprises an inner surface, which is harder than an inner surface of the second introducer at least at the portion of said second curved shape.

* * * * *